United States Patent [19]

Campos

[11] Patent Number: 5,290,217
[45] Date of Patent: Mar. 1, 1994

[54] METHOD AND APPARATUS FOR HERNIA REPAIR

[75] Inventor: Luis I. Campos, Allentown, Pa.

[73] Assignee: Earl K. Sipes, Allentown, Pa.

[21] Appl. No.: 775,692

[22] Filed: Oct. 10, 1991

[51] Int. Cl.⁵ .................. A61F 2/00; A61F 13/00
[52] U.S. Cl. ........................ 600/37; 128/897; 606/151
[58] Field of Search .................. 128/897–899; 600/37; 623/11–14; 606/139, 144, 148, 150, 151, 108, 213

[56] References Cited

U.S. PATENT DOCUMENTS

| | | | |
|---|---|---|---|
| 2,671,444 | 3/1954 | Pease, Jr. | 623/14 |
| 5,122,155 | 6/1992 | Eberbach | 606/213 |
| 5,141,522 | 8/1992 | Landi | 623/13 |

FOREIGN PATENT DOCUMENTS 8204390 12/1982 PCT Int'l Appl. ............ 623/14

Primary Examiner—Lee S. Cohen
Assistant Examiner—John P. Lacyk
Attorney, Agent, or Firm—Eckert Seamans Cherin & Mellott

[57] ABSTRACT

Surgical repairs such as hernia repairs are made via laparoscopic techniques, by attaching a panel or patch of substantially continuous prosthetic material, dimensioned for introduction into a patient via a laparoscopic instrument. The panel is preferably expanded polytetrafluoroethylene (PTFE), provided with a plurality of holes at a peripheral edge for engagement via a surgical clip applicator. The applicator can be used readily to spread the patch over the site of the repair, and to receive the surgical clips which attach the patch to ligamentous structures of the patient. Examples of application of the patch to inguinal hernia repair and diaphragmatic hernia repair are disclosed.

17 Claims, 3 Drawing Sheets

METHOD AND APPARATUS FOR HERNIA REPAIR

BACKGROUND OF THE INVENTION

1. Field of the Invention

This invention relates to repair of hernias and similar defects in the tissues of humans and animals, and in particular to a laparoscopic hernia repair method and a synthetic patch used therefor. The patch is manipulated in the body cavity of the patient and is attached to connective tissues, by engaging the patch at a plurality of peripheral punch holes preliminarily formed in the patch.

2. Prior Art

A hernia is a weakening of the musculofascial tissues defining the structural wall of a body cavity such as the abdomen, resulting in a gap through which tissues can protrude. Typically a sac is formed confining the tissues at the musculofascial defect, which sac protrudes from the plane of the tissue wall. There is a possibility of constriction of the neck of the sac, and life-threatening infection if untreated.

A weakening or separation of the musculofascial tissues due to any cause can develop into a hernia. For example scarring from a previous incision or other trauma of the abdominal wall can develop into a hernia, or a hernia can form at the site of a passage through the musculofascial tissue, the passage becoming enlarged, for example, due to pressure of the viscera during muscular exertion. There are various forms of hernias, the inguinal hernia being a common example wherein the abdominal viscera and peritoneal sac protrude through the floor of the inguinal cavity at the point where the musculofascial tissue is relatively weakened due to the passage of the spermatic duct (in males) or the femoral blood vessels and the round ligament (in females). Another common site of a hernia is the passage of the umbilical cord. Hernias can also develop in the diaphragm, and elsewhere. In general similar problems occur wherever visceral tissues are abutted against a confining wall of tissue which, when weakened for whatever reason, permits the tissues to protrude through the confining wall, where the tissues become subject to constriction and infection or exert potentially dangerous pressure on tissues beyond the wall.

Hernias have been repaired surgically by suturing across the musculofascial defect to draw the opposite sides of the defect together, the sutures bridging across the defect. However, such a repair is not suitable at hernias occurring at the site of a passage for ducts, blood vessels or the like. Moreover, pulling the sides of the defect inwardly results in tension on the musculofascial tissue via the sutures. The site of the sutures defines a weakening of the tissue and leads to a high rate of recurrence of the hernia at the sutured edge of a previous repair.

According to one technique for repairing hernias, tension on the site is reduced by inserting a plug into the opening, for example of rolled polypropylene screen, to reduce the tension applied by the sutures to the musculofascial tissue surrounding the defect, while blocking protrusion of the sac. According to another technique, a patch having sufficient strength to resist the tendency of the sac to protrude is placed over the defect and sutured to the musculofascial tissue. This technique also avoids tension on the musculofascial tissues and has been shown to be successful in minimizing recurrence of the hernia. Various materials have been used in experimental or clinical hernia repairs, including for example polypropylene mesh, Dacron fabric, tantalum gauze, and the like.

Recently, patch repairs of this type have been made using expanded polytetrafluoroethylene or Teflon. The expanded polytetrafluoroethylene (PTFE) form of patch has proved advantageous because it elicits a low foreign body reaction, does not encourage infection, is low in adhesion formation, and does not erode into the abdominal viscera.

Most importantly for permanent repair of hernias, the PTFE material supports fibrous tissue incorporation. Fibroblast intrusions into the porous expanded PTFE material of the patch tend to engage the patch securely as the repair heals. Over time the fibroblasts are replaced by collagen, merging the patch into the surrounding tissue to form a permanent structural repair. An expanded PTFE patch material is available from W. L. Gore & Associates, Inc., Medical Products Division, Flagstaff, Ariz., under the trademark Gore-Tex.

Whereas the hernia originates in the abdominal cavity, laparoscopic diagnosis and repair of hernias is advantageous as it allows repair of the hernia from inside the abdomen without further damage to the musculofascial tissue containing the defect. Laparoscopic hernia repair presents minimal risk, and initial recurrence rates are acceptable for short term follow up. However, the operation is difficult because suturing via trocars and similar laparoscopic instruments, particularly in the inguinal area, requires a great deal of expertise. Although needles and needle holders for use in this manner are available, it is very important to strictly follow an exacting suturing procedure, and normally takes a relatively long time. For example, the surgeon may spend as long as five minutes in setting a single suture.

Hernia repairs have been undertaken by laparoscopic techniques using surgical staples such as the endo-clip, via a clip applicator or surgical stapler. Although there is a risk that a clip can become dislodged, the laparoscopic clip or staple applier facilitates introduction of the clips or staples, and avoids much of the time and difficulty associated with suturing. It would be possible to attach a patch material such as expanded PTFE using surgical staples. The major difficulty remaining in the laparoscopic hernia repair operation is then to position the patch and fasten the patch in place using properly placed clips or staples.

It is important that the patch be accurately positioned in order to fully bridge across the defect to form a good structural repair. In certain instances such as the repair of inguinal hernias at the passage of the spermatic duct or round ligament, the problem is complicated by the need to leave clearance for the duct or ligament, and the need to avoid damage thereto. Obstruction or constriction of the spermatic duct will affect the fertility of the patient. Interference with the round ligament or femoral blood vessels can affect circulation and/or mobility. Accordingly, care must be taken to accommodate the passage while providing a structural bridge across the passage that does not damage or adhere to the tissues passing through.

The present invention modifies the known expanded PTFE patch to facilitate placement and attachment. The patch is provided with a series of punch holes, preferably all around the periphery at an approximate spacing from the edge equal to the span of the surgical staples, and of a diameter approximating the width of one limb of the clip or staple applicator This limb of the applicator engages the patch in the peripheral punch holes, making it readily possible to attach the patch to ligamentous tissues at one point and then to spread the patch over the defect by engaging the applicator in an opposite punch hole. The surgeon thus proceeds to place clips or staples around the periphery of the patch. For inguinal hernia repairs the spermatic duct or round ligament passes under the patch at a punch hole, or two adjacent punch holes, left unfastened.

The invention is useful for laparoscopic patch repairs generally, and is especially useful in connection with hernia repair including inguinal, femoral, diaphragmatic and the like.

SUMMARY OF THE INVENTION

It is an object of the invention to improve the effectiveness of laparoscopic hernia repair patching techniques, and to shorten the time needed therefor, by providing an improved method to manipulate and attach the patch material.

It is a further object to provide an improved surgical patch which includes structures which are readily engaged by relatively small laparoscopic instruments.

It is also an object of the invention to apply laparoscopic hernia repair techniques to surgical patch repairs generally.

It is another object of the invention to provide an improved patch material which with healing becomes structurally embedded in the tissues to which it is attached, by intrusion of fibroblast and collagen material.

These and other objects are accomplished by a surgical repair technique and an improved surgical patch useful therefor. Repairs such as hernia repairs are made laparoscopically by attaching a panel or patch of substantially continuous prosthetic material, dimensioned for introduction into the patient's abdomen or other internal cavity via a laparoscopic instrument. The panel is preferably expanded polytetrafluoroethylene (PTFE), and is provided with a plurality of holes at its peripheral edge for engagement via a surgical clip or applicator or staple applicator. The applicator can be used readily to spread the patch over the site of the repair, and to receive surgical clips or staples which attach the patch to ligamentous structures of the patient. The technique can be applied, for example to inguinal hernia repair, diaphragmatic hernia repair and also to surgical patch repairs generally.

BRIEF DESCRIPTION OF THE DRAWINGS

There are shown in the drawings exemplary embodiments of the invention as presently preferred. It should be understood that the invention is not limited to the precise arrangements and instrumentalities shown and discussed, and is capable of variation in accordance with the scope of the appended claims and their reasonable equivalents. In the drawings.

DETAILED DESCRIPTION OF THE PREFERRED EMBODIMENTS

Figure 1:
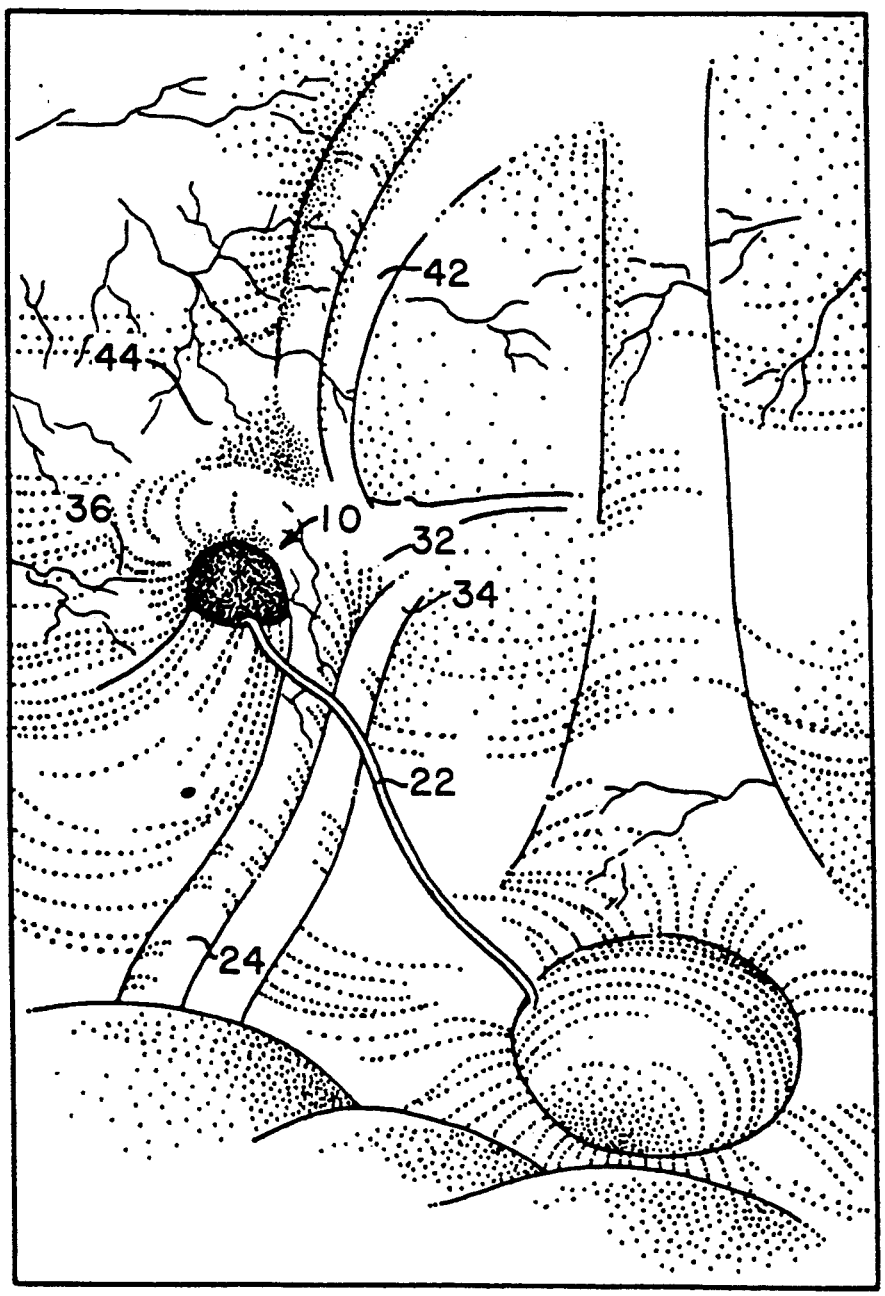
FIG. 1 is an internal view of the inguinal abdominal area as viewed through a laparoscope, showing the anatomy of the area as it appears through a laparoscope.

The invention comprises laparoscopic introduction of a polytetrafluoroethylene (PTFE) patch having a plurality of holes around a peripheral edge, and attachment of the patch over a hernia to provide a permanent structural repair. The peripheral holes facilitate the use of an endo-clip or endo-staple applicator for manipulating and attaching the patch over the defect, the patch being affixed to the ligamentous musculofascial tissue adjacent the defect via surgical staples affixed through the peripheral holes. Applications of the invention to inguinal and diaphragmatic hernias are disclosed as examples.

A study of 10 patients undergoing elective laparoscopic herniorrhaphy was conducted. The technique used consisted of the introduction of an expanded PTFE patch, fenestrated around the edges to facilitate the use of a fastener applicator for surgical clips or staples. Patient tolerance and return to work was favorable. Two cases of prostatitis were identified. There were no recurrences or intra abdominal infections. Follow up of the cases was conducted at six months.

The patch material chosen was the Gore-Tex soft tissue patch, 1 mm thickness and 5.0 cm by 10.0 cm. The patch can be provided initially with peripheral holes, or preferably trimmed to the size and shape of the defect and punched at the periphery prior to introduction. Punching or fenestration of the PTFE patch is possible without fraying the material and without compromising the strength of the patch.

Laparoscopic hernia repair is performed generally with reduced risks to the patient due to the limited trauma associated with laparoscopic techniques as compared to incisional ones, particularly as to the tissues containing the defect. The use of surgical clips to ligate the sac of a hernia intra abdominally was advocated by R. Ger in 1982. More recently, success in connection with laparoscopic cholecystectomy has prompted a variety of attempts to close hernial defects intra-abdominally. The use of clips, Mersilene patches and expanded PTFE have been reported and have been accompanied by reduced recurrence rates. Complications associated with incisional herniorrhaphy are avoided, giving laparoscopy an advantage over traditional repair techniques.

Suturing through the laparoscopic approach requires substantial skill and meticulous attention to technique in order to effectively place and manipulate the needle, especially in the inguinal area. According to the invention an endo-clip or endo-staple applicator facilitates the introduction of clips or staples and the positioning of the clips or staples at the proper position and orientation to minimize the risk of dislodgement. In order to avoid surgeon fatigue during laparoscopic attachment of the patch, and in order to expedite the procedure, an expanded PTFE patch is secured in place using the endo-clip or endo-staple applicator as the means to engage and manipulate the patch. After initial attachment at one or more peripheral holes in the patch, the holes in the patch are helpful as a support for the applicator or staple applicator, allowing rotation of the applicator around a limb inserted in a respective hole, for orienting the applicator in preparation for setting a clip or staple.

Preferably, the patch is premeasured and multiple (8 to 14) circular fenestrations of about 5 mm diameter are created to engage the limb of the clip or staple applicator. Secure placement in the ligamentous anatomical landmarks is then possible. Referring to FIG. 1, anatomical landmarks for laparoscopic hernia repair include the vas deferens or spermatic cord 22 in males (comparable to the round ligament in females), and the inferior epigastric vessels 42. These landmarks are easily identified via laparoscope, as shown in FIG. 1. The hernia 10 is located and classified according to its medial or lateral aspects. Medial to the vas deferens or round ligament are the lacunar ligament 32 and Coopers ligament 34. Lateral to the cord 22 is the inguinal ligament 36. The interfoveolar muscle 44 and tendinous insertion are just lateral and cephalad to the epigastric vessels 42.

Direct hernias (medial to the inferior epigastric vessels 42), indirect hernias (lateral to the inferior epigastric vessels), as well as femoral hernias (below the inguinal ligament 36) all can be repaired through an intra abdominal laparoscopic approach according to the invention.

Attention to the vas deferens or round ligament, and avoidance of the lateral aspect, is important to prevent injuries to the iliac artery and vein 24, since they are localized laterally. The interfoveolar muscle and tendon 44, normally not pertinent to incisional herniorrhaphy, plays an important role according to the invention, both as a landmark and as an anchoring structure for the patch repair.

A standard pneumoperitoneum is created to provide sufficient working room. The peritoneum is suffused through a supra umbilical incision, using a 10 mm cannula. Two lateral punctures are formed, one side using a 10 mm cannula and the other side using a 5 mm cannula. These lateral ports are placed on the semilunar line at the junction with the semicircular line according to Douglas. The 10 mm lateral cannula can be placed either on the right or the left side according to the site of the hernia. Bilateral hernias also can be repaired, with the cannulas on either side. After diagnosis and classification of the hernia, and while the patient is in the Trendelenburg position, the contralateral aspect is examined to determine whether the hernia is bilateral. Once the ring of the hernia defect is visualized, the surrounding peritoneum is incised, avoiding the lateral aspect of the vans deferens or round ligament to prevent iatrogenic injury to the iliac vessels 24.

The hernia sac 12 is identified and treated, for example by tying off the neck of the sac with a loop ligature for indirect hernias or by inserting a spacing Mersilene plug for direct hernias or femoral hernias. The expanded PTFE patch 50 is to be introduced through the 10 mm port. However, prior to insertion of the patch into the intra abdominal cavity the patch is prepared to approximate the size of the hernia ring and fenestrated along its borders. The fenestrations or punch holes 54 can be formed, for example, using a 5 mm punch biopsy clamp of the type used for endocervical biopsies. Holes 54 are preferably regularly spaced around the periphery of the patch, for example spacing each hole about one hole diameter from the next adjacent hole, and inwardly from the peripheral edge by about the span of the surgical staple or endo-clip 70.

The patch 50 is unrolled intra-abdominally and placed on the hernia. The applicator 60 is then introduced. One limb 62 of the applicator is inserted into one of the holes 54 in the patch 50, thereby allowing the corresponding edge of the patch to be positioned via the applicator. The other limb of the applicator is inserted into the corresponding musculofascial structure adjacent the patch at the site of attachment, into the ligamentous structures to which the patch is to be attached, whereupon the applicator is operated to set the clip or staple. The patch 50 is secured respectively to the lacunar ligament 32, Coopers ligament 34, interfoveolar muscles 44 and tendon, and to the inguinal ligament 36.

Proceeding either circumferentially around the patch or in alternating fashion on opposite sides of the patch, the clips or staples are applied. For best results each such fastener is positioned at an angle perpendicular to the edge of the patch and extending perpendicularly downwardly relative to the plane of the patch. The fasteners are preferably distributed evenly in a circumferential manner except at the area lateral to the vas deferens or round ligament. At these locations one or two fenestrations are left unused and the patch is permitted to overly the cord or the round ligament.

The expanded PTFE material is pliable and rolls and unrolls without difficulty. The patch is readily positioned using the clip applicator and stays substantially in position after the initial one or two endo-clips are placed. The clips can be placed on opposite sides to hold the patch in place, thereby spreading the patch over the hernia. Once in place the rest of anchoring clips are placed easily, simply drawing the edge of the patch outwardly and applying a clip at each fenestration used.

Fenestrations of about 5 mm diameter provide easy entry to one limb of the standard laparoscopic endo-clip applicator, with some engagement between the limb and the patch that enables manipulation of the patch. A larger or smaller hole can be used for instruments having a larger or smaller limb. The holes can be placed between about one half and one diameter from the extreme edge of the patch, enabling the clip applicator to readily bridge the distance to the ligamentous tissue adjacent the patch. Whereas one limb of the applicator is engaged in the hole, a rotary motion around the axis of the hole can be accomplished without loosening or displacing the patch. In fact the engagement of the limb in the hole holds the applicator on the axis of the hole while allowing the clip to be placed at the desired angle by rotating the applicator on its inserted limb.

The ligamentous structures hold the patch in place and in conjunction with the patch structurally support the defect defined by the hernia. The center of the patch remains as a solid load bearing unit for resisting reoccurrence. The expanded PTFE material performs substantially the same job as a sutured patch, and does not tend to fray or to leave loose pieces.

Over time, fibroblast intrusion into the patch, and later collagen formation, integrate the patch and the tissue to which it is applied. Tissue healing occurs not only over the patch, but also through the punched holes. This additional engagement of healed tissue with the punched holes or fenestrations provides a more durable repair of the hernia site over the long term.

Six month follow up of the initial 10 cases has shown no recurrences. Two cases of prostatitis were identified, each responding to oral Floxacin within 24 hours. All the patients returned to work, the soonest in 10 days and the latest in two and a half weeks. Patient satisfaction and minimal cosmetic damage due to the puncture wounds was excellent.

This modified technique of patch placement and attachment is an easy, fast and effective way to form a structural hernia repair intra abdominally, particularly in the inguinal area. Although needle holders are available for suturing intra abdominally through a laparoscope, such suturing is time-consuming and demanding as to strict adherence to laparoscopic suturing techniques. Surgeon fatigue is common when multiple sutures are placed. The use of an endo-clip applicator avoids the these drawbacks of suturing, while providing a durable repair.

Expanded PTFE, because its intrinsic structure, provides a pliable material. Fenestration allows the patch to be anchored securely and easily notwithstanding the soft and pliable nature of the material used, giving the surgeon good control of the position of the patch and the clips such that the clips are unlikely to be set at a tangential or oblique angle. The fenestrations permit holding of the patch and at the same time allow the rotational range of applicator motion needed to obtain an optimum angle against the desired structures, preferably extending perpendicularly over the edge of the patch.

Endo-clips when properly placed provide a strong adherence against solid tissue. This method gives an easy way to laparoscopic herniorrhaphy. Is easier to perform and requires only a fenestrated PTFE patch and a conventional endo-clip applicator.

Figure 2:
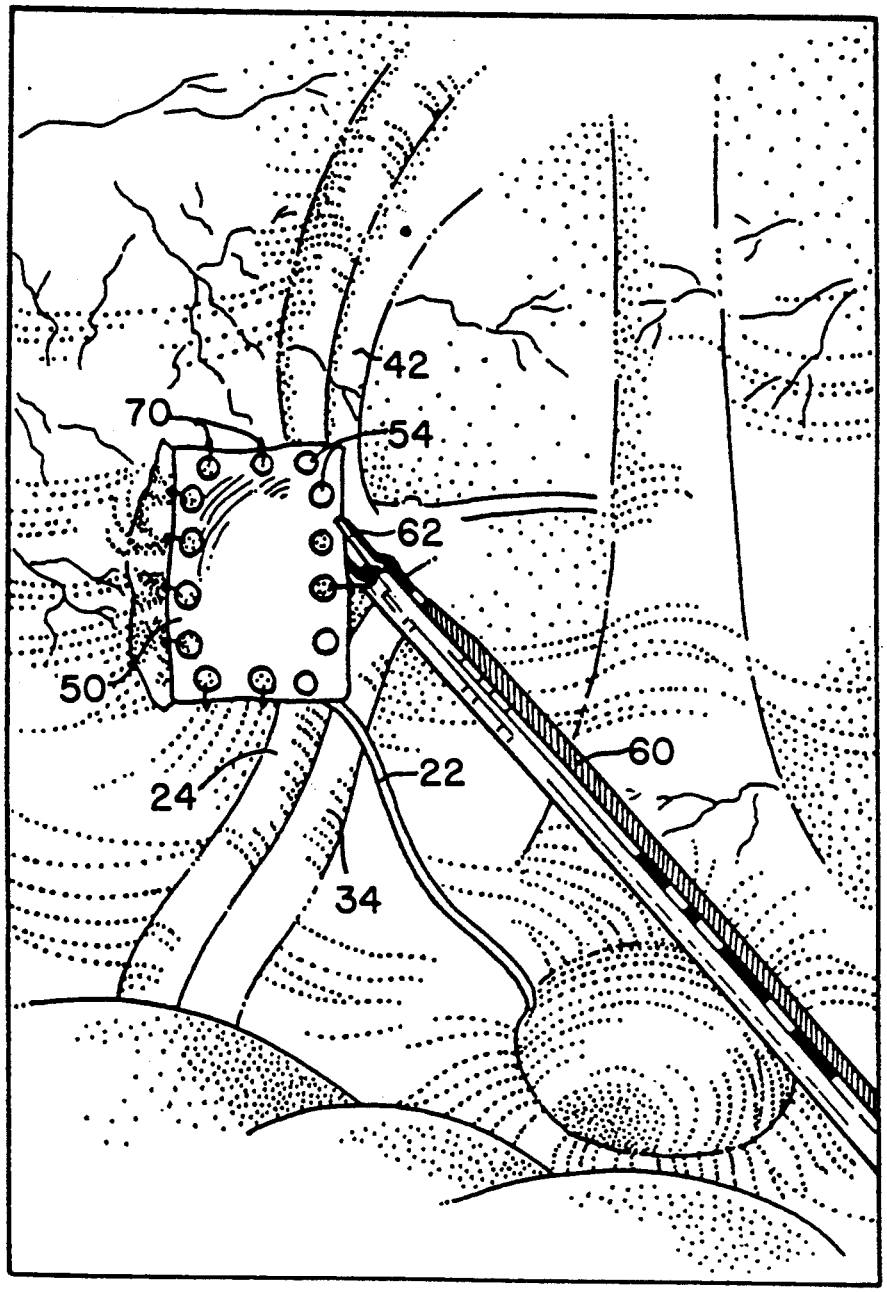
FIG. 2 is a corresponding internal view showing attachment of the patch in place, the patch being shown substantially anchored by endo-clips set by a clip applicator.
Figure 4:
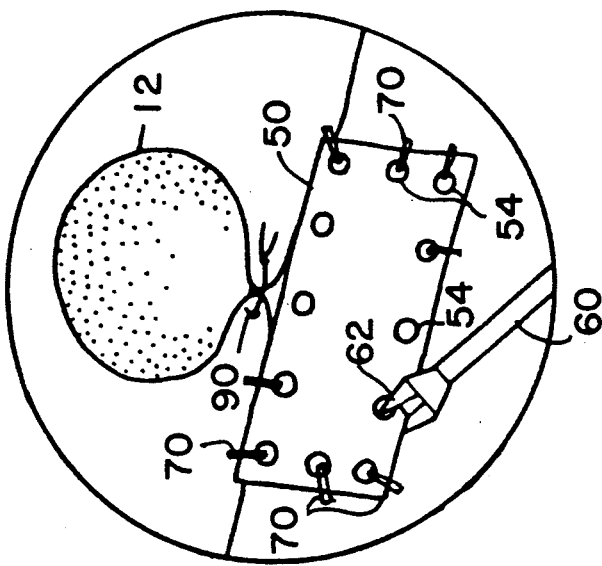
FIG. 4 is a schematic illustration of the diaphragmatic hernia repair in detail, the sac shown ligated.

The invention is applicable to repairs of other hernias and similar defects by intra abdominal application of the PTFE patch. As a second example, a diaphragmatic hernia repair according to the invention was done using a left subcostal trocar insertion with a total of three ports. This operation is illustrated in FIG. 4, using the same reference numerals as in FIGS. 1-3 to identify corresponding elements. The laparoscopic approach to correction of accessible diaphragmatic hernias is helpful due to the ability to visualize the entire abdominal cavity, including the right or left hemidiaphragm. The diaphragm is a relatively vulnerable organ which is easily damaged by direct or indirect trauma. Even a minimal injury to the diaphragm may result in herniation over the years, reported cases documenting herniation problems as much as 15 years following an injury to the diaphragm.

Herniation of the diaphragm is a difficult problem for newborns. Experiments have been conducted into prosthetic grafts for diaphragm repair, and the expanded PTFE patch has been shown be useful due to its capability to become absorbed into tissues by the intrusion of fibroblasts and collagen. However, there is an inherent danger in that laparoscopy normally requires that the operating cavity be suffused with gas to obtain operating space. Tension pneumothorax obviously would be a danger in connection with a herniated diaphragm. It has been discovered, however, that minimally invasive intra abdominal laparoscopic surgery according to the invention can be used to apply a PTFE patch to repair a herniated diaphragm. This is possible where the thoracic cavity or pericardium are not entered.

Figure 3:
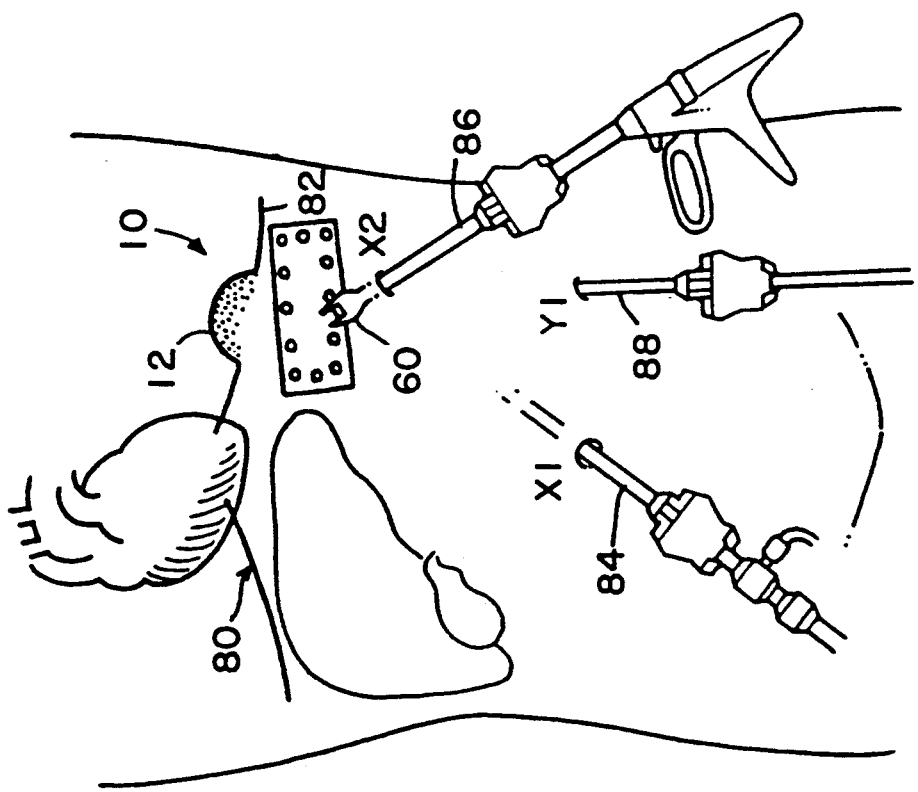
FIG. 3 is a schematic illustration of repair of a diaphragmatic hernia according to the invention.

A 63 year old female had a history of a subtotal gastrectomy with a gastrojejunostomy (Billroth II anastomosis) 21 years prior to admission, to correct a perforated ulcer. The gastric problems were thereby corrected. However approximately two years prior to admission the patient noticed left subcostal pain, localized to the anterior aspect of the lower rib cage at the level of the midaxillary line. The pain would disappear when the patient adopted the right lateral decubitus position or stood up, and the pain by this time prevented sleeping in any other position. An X-ray revealed a mass in the left hemidiaphragm just lateral to the apex of the heart, as shown in FIG. 3. In comparing this X-ray with previous X-rays it became apparent that the mass existed before and was enlarging over time. The mass was round and circumscribed by no air or air/fluid level, and had a consistency which appeared characteristic of adipose tissue.

The symptomatology was consistent with periodic incarceration of a left diaphragmatic hernia. Following a diagnostic laparoscopy a diaphragmatic herniorrhaphy was performed according to the invention, using O-Chromic sutures for ligating the sac and an expanded PTFE patch secured in place according to the invention with an endo-clip applicator.

An open laparoscopy using a modified finger technique and rubber catheter was used in order to provide a safe and gas-sealed pneumoperitoneum. Three trocars were inserted, a first 10 mm trocar 84 at the midline above the umbilicus, a second 10 mm trocar 86 at the midaxillary line on the left subcostal area, and a third 5 mm trocar 88 at the midaxillary line but parallel to the one at the umbilicus. This arrangement is shown in FIG. 3.

Using laparoscopic instruments made by Auto Suture Co., in particular Endo-Dissect and Endo-Shears, lysis of adhesions was accomplished to provide direct exposure of the left hemidiaphragm 82. The defect 12 as measured under direct visualization was approximately 7.5 cm by 3.0 cm.

An expanded PTFE patch 50 was fenestrated at the edges to facilitate engagement with the endo-clip applicator 60 as described above. Using an extracorporeal knot tying technique (Endoknot by Ethicon), two stitches 90 of O-Chromic were applied, including recruiting peritoneal tissue from the edges of the hernia ring. The patch 50 was positioned on the ridges created by tying the hernia, and was secured in place by the endo-clip applicator 60, with clips 70 placed peripherally around the patch at the site, the clips extending substantially perpendicularly from the edges of the patch and perpendicularly into the plane of the diaphragm 80. FIG. 4 illustrates the attachment of the patch over the ligated hernial sac to complete the repair.

The patient's tolerance was excellent throughout the procedure, with no instances of arrythmia or respiratory problems noted. Blood pressure and oxygen saturation remained stable. The defect was 95% closed by the suture 90 tying off the sac 12, and 100% covered by the expanded PTFE patch 50. In the recovery room the patient's symptoms had already disappeared. An X-ray of the chest revealed good mobilization of the operated hemidiaphragm 82 with total reduction of the herniation. The patient was instructed to continue to use the right lateral decubitus position when sleeping, for at least ten days, and was discharged 24 hours after admission. The patient reported total disappearance of her symptoms at a follow up visit a week later, with minimal to no incisional pain.

It is believed that the foregoing case represents an iatrogenically acquired diaphragmatic hernia, possibly due to an originally minor injury to the diaphragm caused by retraction during the subtotal gastrectomy. The hernia, acquired over a period of 20 years, had progressively enlarged. By the time of admission the hernia actually had become life threatening, due to its proximity to the mediastinal structures. The adaptability of laparoscopic surgery to repair such an injury without invasive incisional steps provides a new alternative for dealing with surgical emergencies of this type.

The use of a tension pneumoperitoneum is not a factor when using small penetrating structures to suture the diaphragm as accomplished in the present case. Therefore, it is believed that the fear of inadvertent creation of a tension pneumothorax should not preclude the use of this minimally invasive laparoscopic technique. Moreover, the relative strength of the expanded PTFE patch, and its tendency to become incorporated into the tissue to which it is applied, provide an expectation of good results to this repair over the long term. Strict suturing and tying is not necessary to utilize the benefits of expanded PTFE, which can be attached using the endo-clip applicator, in particular due to the incorporation of the PTFE material into the tissue of the diaphragm over time.

The dramatic cut in operative time, in-hospital stay and concomitant surgical trauma as compared to incisional hernia repair are such that laparoscopic repair of hernias is an advantageous technique. According to the invention, by modifying the patch structure to accommodate attachment tools without the requirement for demanding suturing, the invention enables laparoscopic surgical repairs for defects which previously required more intrusive techniques, and enables wider use of laparoscopy generally.

The invention has been discussed in connection with preferred embodiments and examples. Variations on the preferred embodiments will now become apparent to persons skilled in the art. Whereas the invention is intended to encompass the disclosed embodiments and a range of variations in accordance with this disclosure, reference should be made to the appended claims and their reasonable equivalents in order to assess the scope of the invention in which exclusive rights are claimed.

I claim:

1. A surgical patch, comprising:
a panel of substantially continuous prosthetic material, dimensioned for introduction into a patient, wherein the panel is provided with a plurality of preformed holes at a peripheral edge, whereby the panel can be engaged and manipulated within the patient via the pre-formed holes, prior to attachment to the patient.

2. The surgical patch according to claim 1, wherein the patch comprises expanded polytetrafluoroethylene (PTFE).

3. The surgical patch according to claim 1, wherein the holes are 3-6 mm in diameter and are disposed about one hole diameter from the peripheral edge.

4. The surgical patch according to claim 3, wherein the holes are spaced regularly around the peripheral edge.

5. The surgical patch according to claim 4, wherein the holes are spaced such that the diameter of the holes approximately measures the space between each hole.

6. A method of surgical repair comprising the steps of:
providing a patch defining a panel of substantially continuous prosthetic material with a plurality of pre-formed holes at a peripheral edge;
introducing the patch into a patient;
engaging the patch at the holes at the peripheral edge by engaging a laparoscopic instrument in at least one of the holes; and,
after said engaging step, positioning and then attaching the patch to structures within the patient using fasteners passing through the holes.

7. The method of surgical repair according to claim 6, wherein the holes are engaged via a laparoscopic staple applicator.

8. The method of surgical repair according to claim 7, wherein the surgical repair is a hernia and the patch is attached to ligamentous structures in the patient adjacent a site of the hernia.

9. The method of surgical repair according to claim 8, further comprising leaving at least one of the holes unattached, for passage of a patient duct.

10. The method of surgical repair according to claim 7, further comprising rotating the applicator in a respective one of the holes for aligning a staple.

11. The method of surgical repair according to claim 10, comprising setting said staple substantially perpendicular to a corresponding edge of the patch.

12. The method of surgical repair according to claim 11, comprising setting a plurality of staples, each of the staples being set substantially perpendicular to a corresponding edge of the patch.

13. A method of surgical repair comprising the steps of:
providing a patch defining a panel of substantially continuous prosthetic material with a plurality of pre-formed holes;
introducing the patch into a patient;
engaging the patch at the holes using at least one laparoscopic instrument in at least one of the holes;
positioning the patch to bridge over structures within the patient, using the laparoscopic instrument, and retaining the patch in place; and,
allowing the structures to heal through the holes, thereby assisting in structurally attaching the patch to said structures.

14. The method of surgical repair according to claim 13, wherein said retaining the patch in place comprises affixing the patch to the structures using fasteners passing through the holes.

15. A kit for effecting surgical repair, comprising in combination:
a laparoscopic instrument for introduction into a patient,
a patch including a panel of substantially continuous prosthetic material, dimensioned for introduction into a patient via the laparoscopic instrument, wherein the panel is provided with a plurality of pre-formed holes at a peripheral edge, the holes being dimensioned for engagement via the laparoscopic instrument, whereby the panel can be engaged and manipulated within the patient via the pre-formed holes, prior to attachment to the patient.

16. The kit according to claim 5, wherein the laparoscopic instrument comprises a laparoscopic staple applicator, and the holes are dimensioned for engagement via the laparoscopic staple applicator, the laparoscopic staple applicator comprising a first limb and a second limb.

17. The kit according to claim 16, wherein the holes have a diameter approximating a width of one of the first limb and the second limb of the applicator.

* * * * *

UNITED STATES PATENT AND TRADEMARK OFFICE
CERTIFICATE OF CORRECTION

PATENT NO. : 5,290,217
DATED : March 1, 1994
INVENTOR(S) : Luis Campos, M.D.

It is certified that error appears in the above-indentified patent and that said Letters Patent is hereby corrected as shown below:

In Column 10, line 59, "claim 5," should read --claim 15,--

Signed and Sealed this

Twelfth Day of July, 1994

Attest:

BRUCE LEHMAN

Attesting Officer  Commissioner of Patents and Trademarks